United States Patent
Lynch et al.

(10) Patent No.: US 6,477,402 B1
(45) Date of Patent: Nov. 5, 2002

(54) GUIDEWIRE ADVANCEMENT SYSTEM

(75) Inventors: Arthur S. Lynch, Westwood, MA (US); A. Walter MacEachern, Woburn, MA (US)

(73) Assignee: Arrow International Investment Corp., Wilmington, DE (US)

( * ) Notice: Subject to any disclaimer, the term of this patent is extended or adjusted under 35 U.S.C. 154(b) by 0 days.

(21) Appl. No.: 09/408,383

(22) Filed: Sep. 29, 1999

Related U.S. Application Data

(60) Continuation of application No. 09/069,431, filed on Apr. 29, 1998, now Pat. No. 6,011,988, which is a continuation of application No. 08/455,698, filed on May 31, 1995, now Pat. No. 5,810,012, which is a continuation of application No. 08/221,083, filed on Mar. 31, 1994, now Pat. No. 5,448,993, which is a continuation of application No. 07/993,414, filed on Dec. 21, 1992, now abandoned, which is a continuation of application No. 07/788,049, filed on Nov. 5, 1991, now Pat. No. 5,273,042, which is a continuation of application No. 07/509,500, filed on Apr. 13, 1990, now abandoned, which is a continuation-in-part of application No. 07/372,047, filed on Jun. 27, 1989, now Pat. No. 4,917,094, which is a division of application No. 07/114,451, filed on Oct. 28, 1987, now Pat. No. 4,860,757.

(51) Int. Cl.[7] ............................................. A61M 5/178
(52) U.S. Cl. ...................... 600/434; 600/585; 604/164
(58) Field of Search .................. 600/343, 585; 604/164

(56) References Cited

U.S. PATENT DOCUMENTS

| | | | |
|---|---|---|---|
| 3,416,531 A | 12/1968 | Edwards | 128/348 |
| 3,521,087 A | 7/1970 | Lombardi | 307/237 |
| 3,521,620 A | 7/1970 | Cook | 128/2.05 |
| 3,547,103 A | 12/1970 | Cook | 128/2.05 |
| 3,561,445 A | 2/1971 | Katerndahl et al. | 128/214.4 |
| 3,774,605 A | 11/1973 | Jewett | 128/214.4 |
| 3,826,256 A | 7/1974 | Smith | 128/214.4 |
| 3,835,854 A | 9/1974 | Jewett | 128/214.4 |
| 3,847,140 A | 11/1974 | Ayella | 128/2 M |
| 3,995,628 A | 12/1976 | Gula et al. | 128/214.4 |
| 4,003,369 A | 1/1977 | Heilman et al. | 128/2 M |
| 4,080,706 A | 3/1978 | Heilman et al. | 29/173 |
| 4,160,451 A | 7/1979 | Chittenden | 128/241.4 |
| 4,274,408 A | 6/1981 | Nimrod | 128/214.4 |
| 4,342,313 A | 8/1982 | Chittenden | 128/214.4 |
| 4,397,091 A | 8/1983 | Gustavsson et al. | 33/127 |
| 4,425,908 A | 1/1984 | Simon | 128/1 R |
| 4,534,363 A | 8/1985 | Gold | 128/772 |
| 4,641,649 A | 2/1987 | Walinsky et al. | 128/303.1 |
| 4,650,472 A | 3/1987 | Bates | 604/158 |
| 4,676,249 A | 6/1987 | Arenas et al. | 128/657 |
| 4,724,846 A | 2/1988 | Evans, III | 128/772 |
| 4,726,369 A | 2/1988 | Mar | 128/303 |

(List continued on next page.)

FOREIGN PATENT DOCUMENTS

RU              207358              11/1965

OTHER PUBLICATIONS

Blitt et al. "External Jugular Vein Approach: J–Wire Technique" 1974 pp. 118–120.

Seldinger S., "Catheter Replaceament Of The Needle In Percutaneous Arteriography" pp. 368–376.

Blitt et al. "Central Venous Catheterization Via the External Jugular Vein A Technique Empolying the J–Wire" *JAMA*, 229(7) :817–18 (Aug. 12, 1974).

*Primary Examiner*—Dinh X. Nguyen
(74) *Attorney, Agent, or Firm*—Amster, Rothstein & Ebenstein

(57) ABSTRACT

A guidewire advancement system for inserting catheter guidewires into blood vessels, and more particularly a guidewire dispensing system for the controlled sterile insertion of a coiled spring guidewire to avoid infection of the patient. The system provides for the transmission of an electrical signal by the guidewire to determine its location within the body.

7 Claims, 3 Drawing Sheets

U.S. PATENT DOCUMENTS

| | | | |
|---|---|---|---|
| 4,799,496 A | 1/1989 | Hargreaves | 128/772 |
| 4,813,938 A | 3/1989 | Raulerson | 604/167 |
| 4,844,092 A | 7/1989 | Rydell et al. | 128/772 |
| 4,860,757 A | 8/1989 | Lynch et al. | 128/657 |
| 4,917,094 A | 4/1990 | Lynch et al. | 128/657 |
| 5,125,906 A | 6/1992 | Fleck | 604/171 |
| 5,186,179 A | 2/1993 | MacEachern | 128/772 |
| 5,273,042 A | 12/1993 | Lynch et al. | 128/657 |
| 5,438,993 A | 8/1995 | Lynch et al. | 128/657 |
| 5,448,993 A | 9/1995 | Lynch et al. | 128/657 |

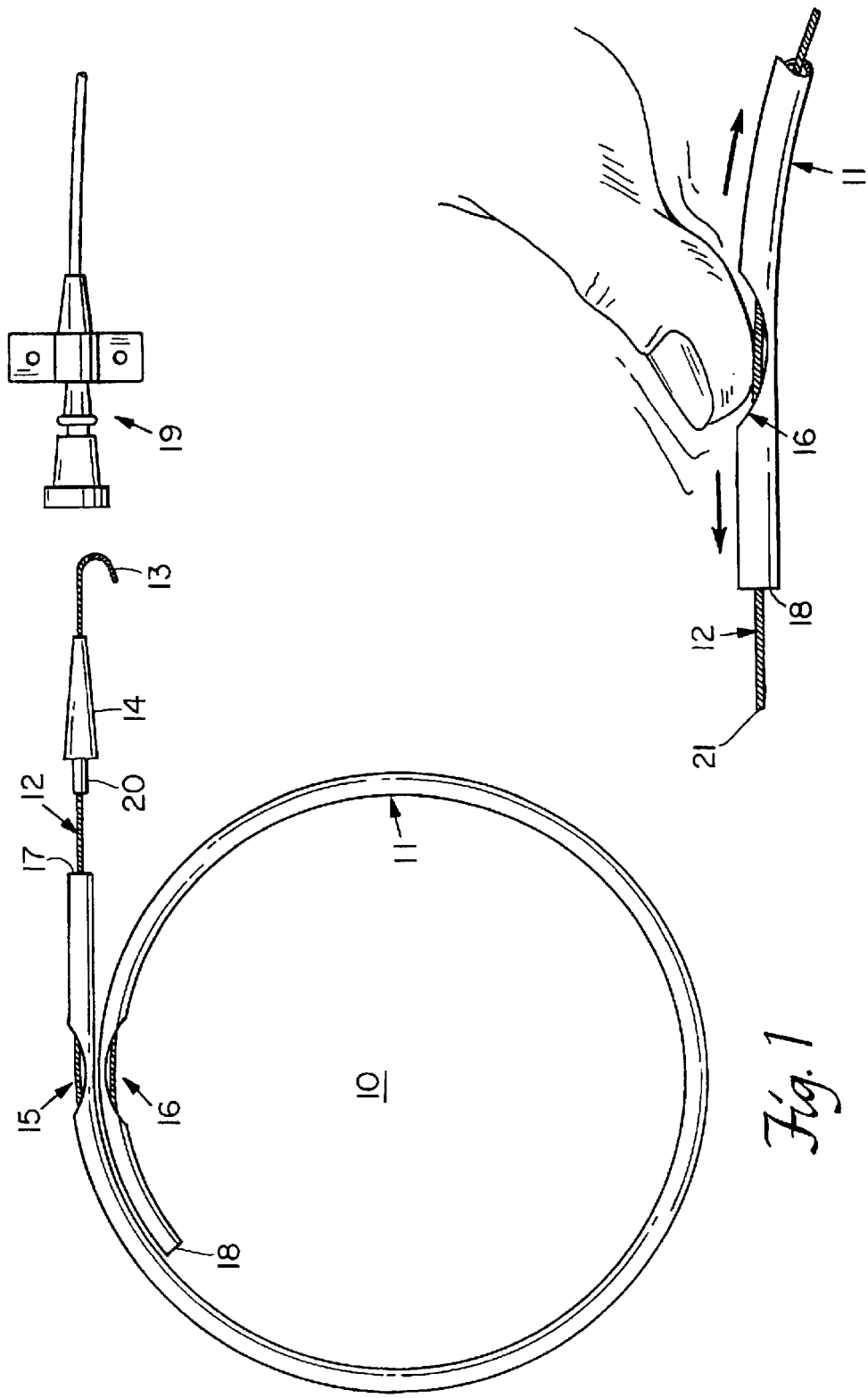

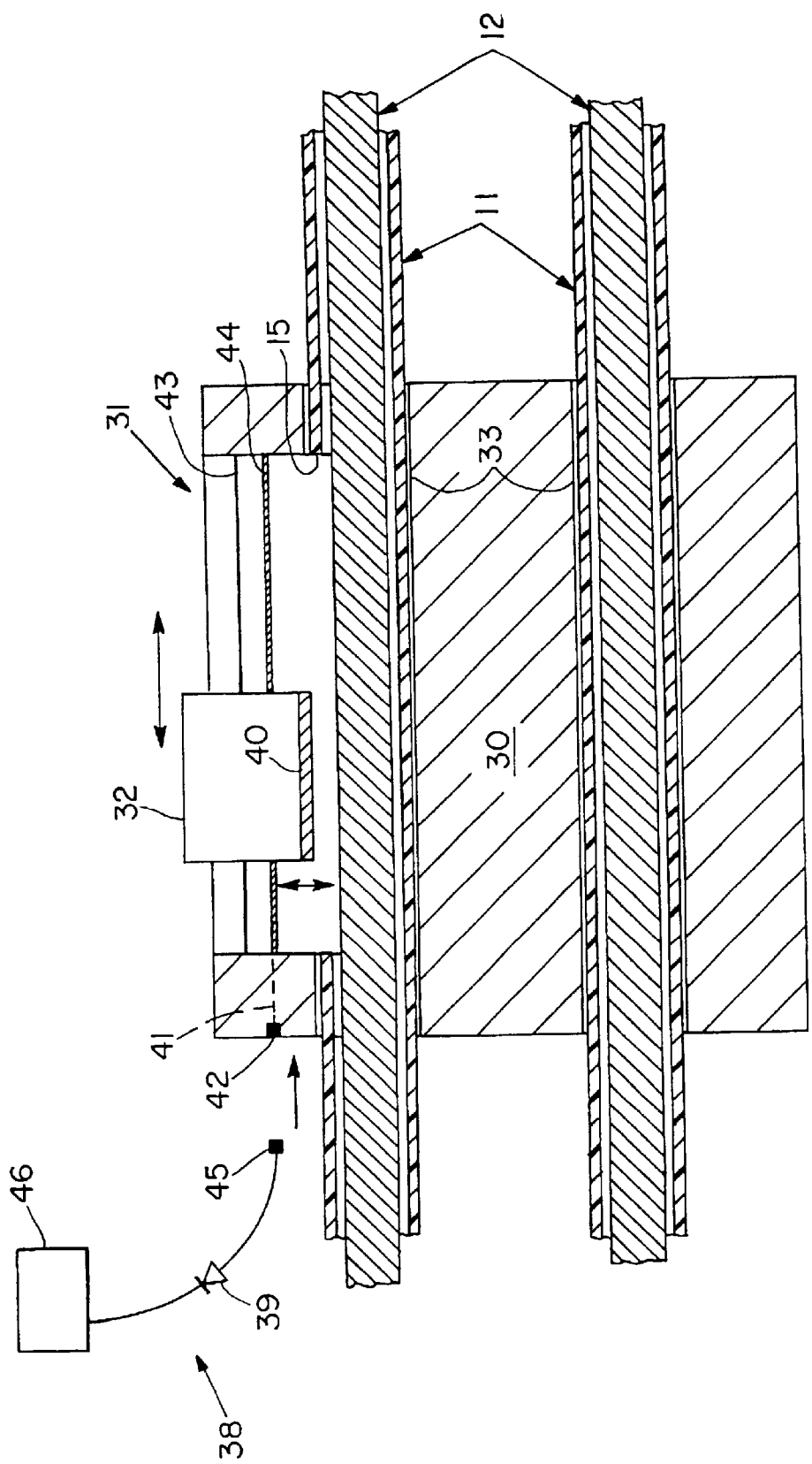

GUIDEWIRE ADVANCEMENT SYSTEM

RELATED APPLICATION(S)

This application is a continuation of application Ser. No. 09/069,431 filed Apr. 29, 1998, now U.S. Pat. No. 6,011,988 a continuation of application Ser. No. 08/455,698 filed May 31, 1995, now U.S. Pat. No. 5,810,012, which is a continuation of application Ser. No. 08/221,083 filed Mar. 31, 1994, now U.S. Pat. No. 5,448,993, which is a continuation of application Ser. No. 07/993,414 filed Dec. 21, 1992, now abandoned, which is a continuation of application Ser. No. 07/788,049 filed Nov. 5, 1991, now U.S. Pat. No. 5,273,042 which is a continuation of U.S. application Ser. No. 07/509,500 filed on Apr. 13, 1990, now abandoned, which is a continuation-in-part of U.S. application Ser. No. 07/372,047 filed on Jun. 27, 1989, now U.S. Pat. No. 4,917,094, which was a divisional application of U.S. application Ser. No. 07/114,451 filed on Oct. 28, 1987, now U.S. Pat. No. 4,860,757, the entire contents of the above applications are incorporated herein by reference.

BACKGROUND OF THE INVENTION

The invention relates to devices for the insertion of catheter guidewires into blood vessels. A guidewire is inserted so that a catheter, which is coaxially engaged with the guidewire, may be inserted into the. blood vessel. The guidewire is then withdrawn, and the catheter is ready for further positioning and use. It is imperative that guidewires be inserted without contamination of the sterile field to avoid unnecessary infection of the patient.

Guidewires are generally comprised of a coiled spring guide with a distal tip and one or more wires running longitudinally within the spring. Such guidewire constructions are disclosed in U.S. Pat. Nos. 4,003,369 and 4,676,249. Catheters are generally hollow, flexible tubes used to convey liquids or other instruments to a desired location in the body.

Existing systems for guidewire insertion suffer from continued problems arising from the lack of ease in manipulation and the exposure during insertion to a non-sterile environment. Normally, a guidewire is removed completely from its package prior to use, is wound in the physician's hand and inserted through a needle extending into the patient's artery, or through a cannula into some other body cavity. Three or more hands are required to hold the needle stationary while the "J" guidewire is pulled through a straightener, then pushed through the port in the needle. The inadvertent extension of the guidewire prior to insertion and the awkwardness of manipulation during insertion leads to contamination of the sterile field and the patient's blood stream. It is also desirable that the physician or operator be able to tactilely sense the progress of the guidewire tip during insertion to insure better control.

SUMMARY OF THE INVENTION

A catheter guidewire is packaged for use in a hollow tube or casing which maintains a sterile environment for the guidewire prior to use. The guidewire is displaceable through an outlet at one or both ends of the tube for insertion into the desired artery or body cavity.

An aperture in the casing is located adjacent to the outlet so as to provide access to the guidewire surface. By applying a lateral frictional force to the surface of the guidewire in the direction of the outlet, the guidewire can be displaced through the narrow tube and the outlet.

A second tube attached to the outlet and disposed to receive the guidewire as it exits the casing can be used to straighten a "J" guidewire prior to entering a canal through a needle or cannula. In a preferred embodiment of the invention, the aperture for frictionally displacing the guidewire can be located in the straightening tube. The invention thus provides a means for maintaining a sterile environment during storage and insertion of the guidewire. Only one hand is necessary to operate the dispensing mechanism while the desired sensitivity to guidewire placement in maintained.

In another preferred embodiment, a moveable member is positioned over the aperture to maintain a sterile environment for the guidewire while at the same time providing the frictional force to displace the guidewire. This moveable member can be hand actuated rollers or a slidable bar or any other suitable mechanical device that maintains the tactile sense of the operator with regard to directing the guidewire through the system. The member which can be manually depressed to frictionally engage the guidewire surface. The moveable member can also be placed in a housing used to hold the two ends of the casing.

One embodiment of the system provides for the transmission of an electrocardiographic signal through the guidewire to determine the position of the distal end of the guidewire that has been inserted into a body canal. The housing that holds the frictionally engaging member referenced above is positioned about the aperture and used to transmit an internally generated electrical signal onto the conductive guidewire element.

The above, and other features of the invention, including various novel details of construction and combination of parts, will now be more particularly described with reference to the accompanying drawings and pointed out in the claims. It will be understood that the particular guidewire advancement system embodying the invention is shown by way of illustration only and not as a limitation of the invention. The principle features of this invention may be employed in varied embodiments without departing from the scope of the invention. For example, the device can be utilized in the catheterization of any body cavity or artery, or alternatively in any veterinary applications involving catheterization procedures.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 illustrates a plan view of the guidewire system generally;

FIG. 2 schematically illustrates a close up view of the guidewire aperture operated by hand;

FIG. 6 is a magnified cross-sectional view illustrating the use of an external monitor that displays an internally generated electrical signal transmitted along the guidewire that is employed in determining the position of the guidewire.

DETAILED DESCRIPTION OF THE INVENTION

Figure 3:
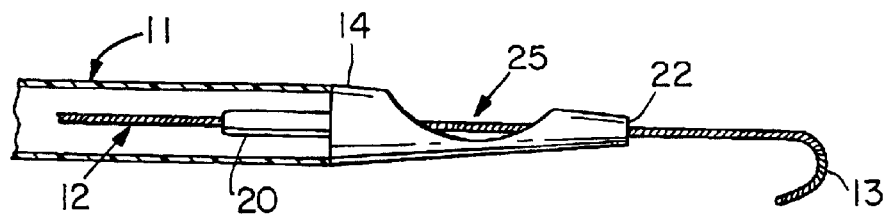
FIG. 3 illustrates a plan view of an alternative embodiment where the aperture is located in the guidewire straightener.

A preferred embodiment of the guidewire advancement system 10 is illustrated in FIG. 1. A flexible hollow tube 11 can be disposed in the shape of a curve or loop(s) as depicted to facilitate ease of operation. A guidewire 12 of standard coiled spring design is slidably inserted into tube 11. The guidewire 12 can enter or exit tube 11 through either of the two open ends 17 and 18. The guidewire 12 is inserted into a vein or artery through a needle, or canal or cavity by a cannula 19.

One end of the guidewire 12 can be formed in the shape of a flexible "J" 13. The "J" 13 may be straightened by pulling the end of the guidewire bearing the "J" back into the straightening element 14. The straightener 14 has a narrow hollow tube to which the "J" must conform upon entry therein. The straightener 14 is attached to tube 11 by inserting a small diameter portion 20 of straightener 14 into the port 17. The outer diameter of portion 20 is chosen so that it fits snugly into the hollow tube 11 at 17. The purpose of the "J" 13 is to permit the guidewire operator to more precisely direct the insertion of the guidewire to the precise arterial location desired. As the guidewire proceeds along the inside of an artery there are commonly two or more paths for it to follow. The operator, using the tension in the straightened "J" to return to its preferred shape, can direct the guidewire down the desired artery path. Simply by rotating the guidewire within the cannula 19, the "J" 13 will be. redirected as desired.

Existing guidewire packages typically involve the complete removal of the guidewire from the tubing in which they are stored before use. This often exposes the guidewire to non-sterile environments thereby risking the infection of the patient when the exposed guidewire is inserted into the bloodstream.

The present invention claims. the use of apertures 15 and 16 located adjacent the two end ports 17 and 18. These apertures provide access to the guidewires 12 so that it may be inserted into the bloodstream without being first removed from its storage tube 11 or jacket. The apertures and 16 permit the use of the guidewire to be confined within the sterile field thereby substantially reducing the risk of unnecessary infection.

FIG. 2 illustrates how the apertured guidewire system may be operated by hand. By inserting his or her thumb into the aperture 16, the operator frictionally engages the guidewire 12, and can either advance or retract it as shown. This design permits one handed operation that is sensitive to guidewire placement. Aperture 16 may be used, as opposed to aperture 15 in FIG. 1, where the operator prefers to use the straight end 21 of the guidewire through port 18, instead of the "J" shaped end 13.

FIG. 3 illustrates another preferred embodiment of the invention where the straightener 14 is provided with aperture 25. The guidewire 12 can be manipulated through aperture 25 directly adjacent the guidewire exit point 22, instead of further back along the tube 11 at aperture 15 in FIG. 1.

Figure 4:
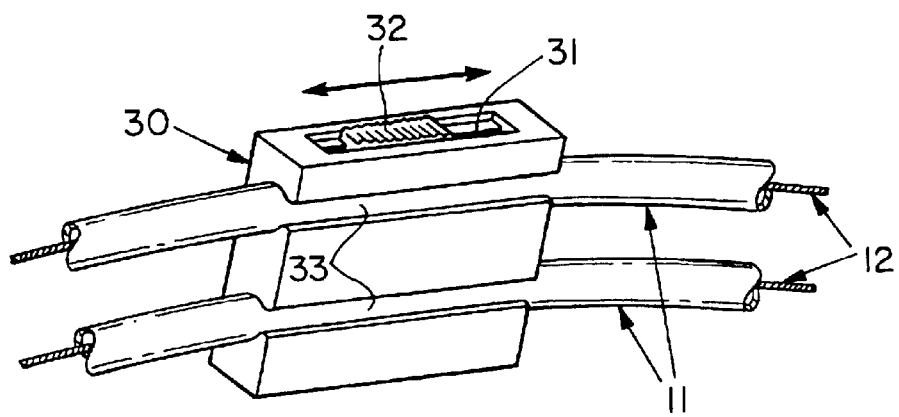
FIG. 4 illustrates a perspective view of a guidewire advancement system using a slidable bar.
Figure 5:
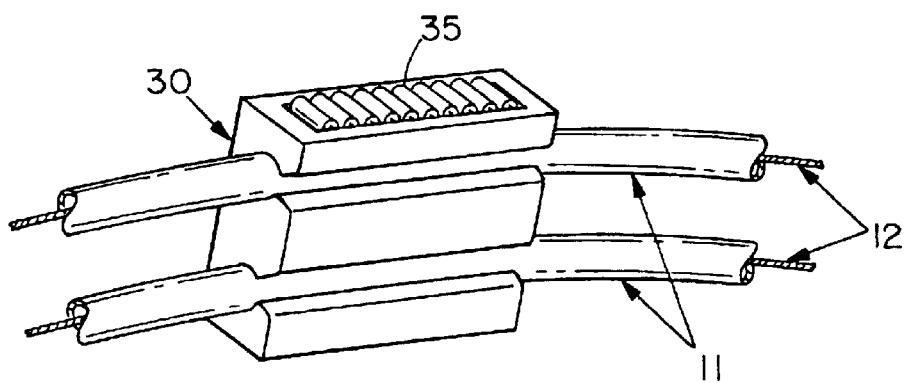
FIG. 5 illustrates a perspective view of a guidewire advancement system using rollers.

To further isolate the guidewire from exposure to non-sterile environments the apertures 15 and 16 can be enclosed with an element 30 as illustrated in FIGS. 4 and 5. The element 30 is used to hold the two ends of the tube 11 in the shape of a loop as shown in FIG. 1. The two ends of tube 11 are both snapped into the two parallel partially open tubes 33 extending through element 30 such that the apertures 15 and 16 (not shown) are completely enclosed.

A rectangular opening 31 can be made in the element 30 opposite the apertures (not shown) in tube 11. A slidable cam or bar 32 may be fitted into opening 31 that can be manually depressed to frictionally engage the guidewire. By positioning the cam 32 at one end of the opening 31, the guidewire 12 may be advanced through the tube 11 in one direction. By depressing the cam 32 to engage the guidewire, the operator slides the cam 32 to the other end of the opening 31, releasing the cam 32 from its depressed position, moving the cam 32 back to its position at the opposite end of the opening 31, and then repeating this sequence of steps until the guidewire is in the desired location.

FIG. 5 illustrates a further embodiment of the invention in which a number of rollers 35 may be depressed to engage the guidewire 12 through an enclosed aperture in tube 11. These rollers frictionally engage the guidewire 12 such that their manually actuated rotation causes the guidewire to be pushed through tube 31 for insertion into the artery.

Both the cam 32 of FIG. 4 and the rollers 35 of FIG. 5 may be held within member 30 by resilient means which lift the cam 32 or rollers 35 off of the guidewire 12 when not manually depressed against it by the operator. This resilient means renders the cam 32 or rollers 35 easier to cycle a number of times to fully extend the guidewire.

Another preferred embodiment is illustrated in the magnified cross sectional view of FIG. 6. As in FIG. 4, a conductive guidewire 12 is displaceable through tubing 11, that is held by a housing 30. A slideable bar 32 is configured to move back and forth within an opening 31. The bar 32 is supported by a track 43. A lower portion of the track 43 incorporates a conductive lining 44 in conductive contact with a conductive pad 40 mounted on the underside of bar 32. The track 43 and attached lining 44 are flexible thereby permitting the bar 32 to be depressed manually by the operator such that the pad 40 comes in contact with the guidewire through aperture 15 of tube 11. The lining 44 is in conductive contact with an outlet 42 by wire 41. The outlet 42 is mated with an external plug 45 connected to a monitoring circuit 38 including a diode 39 and an external monitor 46. The diode 39 prevents any back current from being transmitted from circuit 38 into the guidewire which can be harmful to the patent. The electrical signal generated by an internal organ such as the human heart transmits a signal through the guidewire 12 to pad 40 when the bar 32 is depressed. This signal is transmitted through the distal tip of the guidewire that has been inserted into a bodily canal or artery to determine the location of the distal tip within the body being catheterized. As the tip approaches the heart muscle, it transmits the electrical current generated about the heart along the guidewire through the engaging means of the housing to be displayed by the monitor 46. This system provides for a more precise positioning of the guidewire as well as the catheter while at the same time providing for the sterile insertion of the guidewire.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A guidewire advancement device comprising:
   a flexible guidewire having a curved distal end;
   a casing for holding the guidewire, the casing being formed in a loop and having an outlet;
   a straightening element having a guidewire exit point and a tube portion adjacent the guidewire exit point, the tube portion formed to straighten the curved distal end of the guidewire as the guidewire is passed through the tube portion, the straightening element being connected to the casing at the outlet of the casing; and
   an aperture on said straightening element to expose a portion of the guidewire and through which the portion of the guidewire can be manually engaged, the aperture being located between the outlet of the casing and the guidewire exit point of the straightening element.

2. The guidewire advancement device of claim 1 further comprising a second aperture on the casing.

3. The guidewire advancement device of claim 1 further comprising a retaining element for retaining the flexible tube in the shape of a loop.

4. The guidewire advancement device of claim 1 further comprising a cannula that receives the guidewire from the straightener.

5. A method of advancing a flexible guidewire to a desired intracorporeal location using only one hand, comprising the steps of:
   (A) providing (i) a flexible guidewire having a curved distal end, (ii) a casing holding the guidewire, the casing being formed in a loop and having an outlet for the guidewire and a sidewall, and (iii) a straightening element having a guidewire exit and a tube portion adjacent the guidewire exit point, the tube portion being configured and dimensioned to straighten the curved distal end of the guidewire as the guidewire is passed through the tube portion, the straightening element being adjacent the guidewire exit point;
   the casing sidewall defining an aperture exposing a portion of the guidewire and through which the exposed length of the guidewire can be manually engaged, the aperture being located between the outlet of the casing and the tube portion of the straightening element; and
   (B) with only one hand grasping the casing sidewall and with at least one finger of the hand manually engaging the exposed portion of the guidewire through the casing aperture, advancing the guidewire through the casing and into the desired intracorporeal location.

6. A method of advancing a flexible guidewire to a desired intracorporeal location using only one hand, comprising the steps of:
   (A) providing a flexible guidewire and a casing holding the guidewire, the casing being formed in a loop, having a portion extending beyond the loop to a guidewire exit port and defining an aperture in the casing to expose a length of the guidewire and through which aperture the length of the guidewire can be manually engaged in order to displace the guidewire relative to the exit port, the aperture being positioned near the exit port; and
   (B) with only one hand grasping the casing and with at least one finger of the hand manually engaging the exposed portion of the guidewire through the casing aperture, advancing the guidewire through the casing and into the desired intracorporeal location.

7. A method of advancing a flexible guidewire to a desired intracorporeal location using only one hand, comprising the steps of:
   (A) providing (i) a flexible guidewire having a curved distal end, (ii) a casing for holding the guidewire, the casing being formed in a loop, having a portion extending beyond the loop to a guidewire exit port and defining an aperture in the casing sidewall to expose a length of the guidewire and through which aperture the length of the guidewire can be manually engaged in order to displace the guidewire relative to the exit port, the aperture being positioned near the exit port; and (iii) a straightener connected to the casing at the exit port which receives the guidewire displaced through the casing, the straightener including a straightener tube having a length and diameter to straighten the curved distal end of the guidewire; and
   (B) with only one hand grasping the casing sidewall and with at least one finger of the hand manually engaging the exposed portion of the guidewire through the casing aperture, advancing the guidewire through the casing and into the desired intracorporeal location.

* * * * *

(12) EX PARTE REEXAMINATION CERTIFICATE (5875th)
United States Patent
Lynch et al.

(10) Number: US 6,477,402 C1
(45) Certificate Issued: Aug. 28, 2007

(54) GUIDEWIRE ADVANCEMENT SYSTEM

(75) Inventors: Arthur S. Lynch, Westwood, MA (US); A. Walter MacEachern, Woburn, MA (US)

(73) Assignee: Arrow International Investment Corp., Wilmington, DE (US)

Reexamination Request:
No. 90/006,982, Mar. 25, 2004

Reexamination Certificate for:
Patent No.: 6,477,402
Issued: Nov. 5, 2002
Appl. No.: 09/408,383
Filed: Sep. 29, 1999

Related U.S. Application Data

(60) Continuation of application No. 09/069,431, filed on Apr. 29, 1998, now Pat. No. 6,011,988, which is a continuation of application No. 08/455,698, filed on May 31, 1995, now Pat. No. 5,810,012, which is a continuation of application No. 08/221,083, filed on Mar. 31, 1994, now Pat. No. 5,448,993, which is a continuation of application No. 07/993,414, filed on Dec. 21, 1992, now abandoned, which is a continuation of application No. 07/788,049, filed on Nov. 5, 1991, now Pat. No. 5,273,042, which is a continuation of application No. 07/509,500, filed on Apr. 13, 1990, now abandoned, which is a continuation-in-part of application No. 07/372,047, filed on Jun. 27, 1989, now Pat. No. 4,917,094, which is a division of application No. 07/114,451, filed on Oct. 28, 1987, now Pat. No. 4,860,757.

(51) Int. Cl.
*A61M 5/00* (2006.01)

(52) U.S. Cl. .................. 600/434; 600/585; 604/164.01
(58) Field of Classification Search ...................... None
See application file for complete search history.

(56) References Cited

U.S. PATENT DOCUMENTS 4,425,908 A    1/1984   Simon

FOREIGN PATENT DOCUMENTS

JP       59-67968       4/1984
SU       207358       * 11/1965

* cited by examiner

*Primary Examiner*—Bibhu Mohanty

(57) ABSTRACT

A guidewire advancement system for inserting catheter guidewires into blood vessels, and more particularly a guidewire dispensing system for the controlled sterile insertion of a coiled spring guidewire to avoid infection of the patient. The system provides for the transmission of an electrical signal by the guidewire to determine its location within the body.

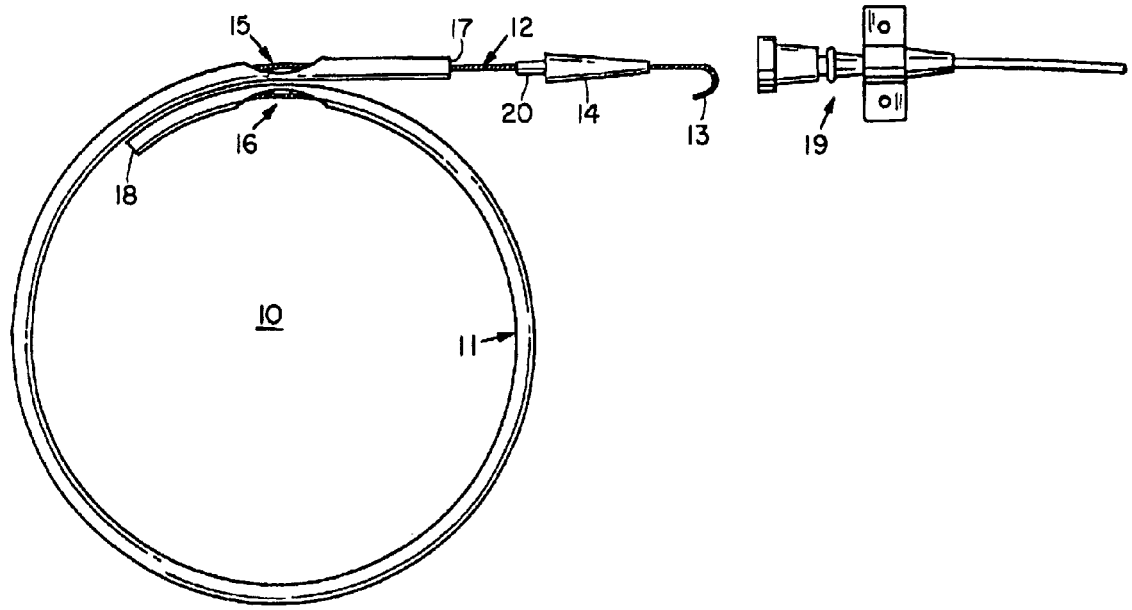

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 5–6, 7 are determined to be patentable as amended.

Claims 2–4, dependent on an amended claim, are determined to be patentable.

1. A guidewire advancement device comprising:
   a flexible guidewire having a curved distal *J* end;
   a casing for holding the guidewire, the casing being formed in a loop and having an outlet;
   a straightening element having a guidewire exit point and a tube portion adjacent the guidewire exit point, the tube portion formed to straighten the curved distal end of the guidewire as the guidewire is passed through the tube portion, the straightening element being connected to the casing at the outlet of the casing; and
   an aperture on said straightening element to expose a portion of the guidewire and through which the portion of the guidewire can be manually engaged, the aperture being located between the outlet of the casing and the guidewire exit point of the straightening element.

5. A method of advancing a flexible guidewire to a desired intracorporeal location using only one hand, comprising the steps of:
   (A) providing (i) a flexible guidewire having a curved distal *J* end, (ii) a casing holding the guidewire, the casing being formed in a loop and having an outlet for the guidewire and a sidewall, and (iii) a straightening element having a guidewire exit and a tube portion adjacent the guidewire exit point, the tube portion being configured and dimensioned to straighten the curved distal end of the guidewire as the guidewire is passed through the tube portion, the straightening element being adjacent the guidewire exit point; the casing sidewal defining an aperture exposing a portion of the guidewire and through which the exposed length of the guidewire can be manually engaged, the aperture being located between the outlet of the casing and the tube portion of the straightening element; and
   (B) with only one hand grasping the casing sidewall and with at least one finger of the hand manually engaging the exposed portion of the guidewire through the casing aperture, advancing the guidewire through the casing and into the desired intracorporeal location.

6. A method of advancing a flexible guidewire to a desired intracorporeal location using only one hand, comprising the steps of:
   (A) providing a flexible guidewire *having a distal J end,* and a casing holding the guidewire, the casing being formed in a loop, having a portion extending beyond the loop to a guidewire exit port and defining an aperture in the casing to expose a length of the guidewire and through which aperture the length of the guidewire can be manually engaged in order to displace the guidewire relative to the exit port, the aperture being positioned near the exit port; and
   (B) with only one hand grasping the casing and with at least one finger of the hand manually engaging the exposed portion of the guidewire through the casing aperture, advancing the guidewire through the casing and into the desired intracorporeal location.

7. A method of advancing a flexible guidewire to a desired intracorporeal location using only one hand, comprising the steps of:
   (A) providing (i) a flexible guidewire having a curved distal *J* end, (ii) a casing for holding the guidewire, the casing being formed in a loop, having a portion extending beyond the loop to a guidewire exit port and defining an aperture in the casing sidewall to expose a length of the guidewire and through which aperture the length of the guidewire can be manually engaged in order to displace the guidewire relative to the exit port, the aperture being positioned near the exit port; and (iii) a straightener connected to the casing at the exit port which receives the guidewire displaced through the casing, the straightener including a straightener tube having a length and diameter to straighten the curved distal end of the guidewire; and
   (B) with only one hand grasping the casing sidewall and with at least one finger of the hand manually engaging the exposed portion of the guidewire through the casing aperture, advancing the guidewire through the casing and into the desired intracorporeal location.

\* \* \* \* \*